May 3, 1955 E. T. SANDALL Plant Pat. 1,389
ALMOND TREE
Filed July 6, 1954
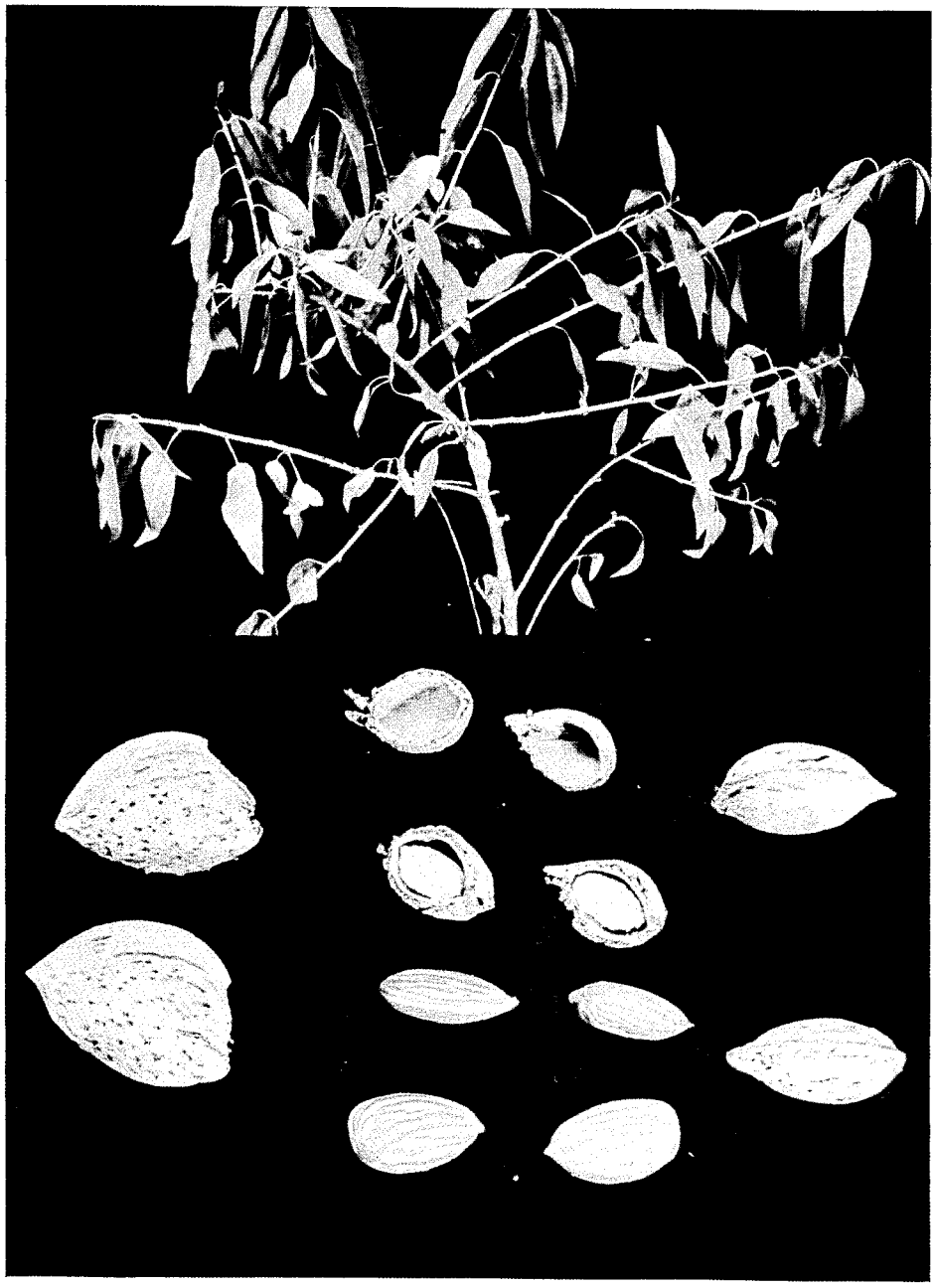
Inventor.
E. T. Sandall
By: Robb & Robb
attorneys.

United States Patent Office

Plant Pat. 1,389

Patented May 3, 1955

1,389

ALMOND TREE

Ernest T. Sandall, Escalon, Calif.

Application July 6, 1954, Serial No. 441,697

1 Claim. (Cl. 47—62)

The present invention relates to a new and distinct variety of almond tree which originated as a bud sport of the variety known as "Nonpareil" (unpatented). The sport was originally discovered by me on my cultivated property at Escalon, California, my attention having been initially drawn thereto by the fact that a small branch on one of my "Nonpareil" almond trees came into full bloom after all of the other blossoms on the tree had fallen. At that time, I suspected that this late-blooming branch was dying, but by carefully and continuously observing the same, I found that it continued to grow, and each year, it continued to bloom late, and in fact, later than any other variety known to me, as well as to bear nuts somewhat different from those of the "Nonpareil" variety.

Continued observations of the nuts indicated that the nuts of my new sport ripen approximately five days later than those of the "Nonpareil" variety, usually during the latter part of August, at Escalon, California, and the nut shells were smoother and harder than those of the "Nonpareil" variety. Otherwise, the size, shape and color of the flowers of my new variety, as well as the foliage and habits of growth of the new variety, are substantially identical with the characteristics of the variety "Nonpareil," and the kernels of the nuts were found to be also substantially identical with those of "Nonpareil."

After continued observations of my new variety for a number of years, I became convinced that the late-blooming characteristic thereof was an important and very desirable attribute, since the new variety would have a much better chance of escaping frosts, which is one of the important considerations in selecting varieties for commercial plantings; also, the greater hardness and smoothness of the nut shells of my new variety constituted important commercial advantages from the standpoint of improved handling, packing and shipping qualities of the nuts.

With the foregoing in mind, I undertook to asexually reproduce the new sport by grafting, as performed by me at Escalon, California, and continued observations of the asexual reproductions show that the aforementioned novel characteristics and distinctions come true to form and are established and transmitted through succeeding propagations.

The accompanying drawing shows a typical specimen limb section of my new variety of almond tree, indicating the foliage and branching habits thereof, and also typical specimens of the nuts, with the nuts shown in plan, in elevation and in transverse cross-section both with and without the kernels, and typical kernels also being shown in plan and in elevation.

The following is a detailed description of my new variety, as based upon observations made from specimens grown at Escalon, California, with color terminology in accordance with Maerz & Paul Dictionary of Color, 1930 ed., except where general color terms of ordinary dictionary significance are obvious:

Parentage: Sport of "Nonpareil."

Propagation: Holds its distinguishing characteristics through succeeding propagations by grafting.

Maturity season: About five days later than the variety "Nonpareil"; usually during the latter part of the month of August.

Tree: Medium size; medium strength; hardy; very productive.

*Growth.*—Average to medium vigor. Limbs—medium; between upright and spreading.

*Color of bark.*—Light Gray, underlaid by Dark Reddish Gray which becomes visible on older wood and on larger branches.

Foliage: Medium abundance; tends to be somewhat open.

*Leaves.*—Substantially identical with those of "Nonpareil"; medium size; from about ¾″ x 2″ to 1″ x 3½″, but somewhat larger on vigorous shoots; lanceolate; crenate margins.

Bloom: Substantially identical with that of "Nonpareil"; medium to fairly heavy quantity.

*Color.*—Very Light Pink in bud, Plate I, B1, although slightly deeper at margins; fades to White as the blossom opens, although the extreme base of petal remains reddish.

*Blooming period.*—About two weeks after "Nonpareil," and about one week after the unpatented variety "Texas" (Mission).

Nuts: Well-distributed; borne laterally on short twigs; ripen evenly; hull rounded particularly on ventral edge, with ventral suture depressed and with dehiscence on ventral suture.

*Ripening period.*—About 5 days after "Nonpareil"—usually last of August.

*Tenacity.*—Hang well on tree.

*Size.*—From 1⅜″ to 1½″ long x ⅞″ to 1″ wide.

*Form.*—Broad ovate; somewhat plump.

*Shell.*—Classifies as soft shell; medium thickness; smooth; outer shell is entire; inner shell is fairly soft; well-sealed; cracks and releases easily. Color—Light Straw, Plate 9, G-5.

*Pits.*—Medium size; fairly numerous; rounded; fairly deep.

*Base.*—Round; ventrally oblique.

*Apex.*—Obtuse, with a short, sharp tip.

*Wing (fin).*—Prominent; extends full length of ventral side.

*Weight.*—Average about 225 to 250 nuts per pound.

*Kernel.*—Size—averages about 15/16″ x 9/16″ x 5/16″; average weight approximately 25 kernels per oz.; kernels average approximately 55% of nut by weight. Form—oval, but tapering slightly toward apex; medium thickness; few double kernels. Base—tends to be truncate, particularly on dorsal shoulder; rounded on ventral shoulder. Apex—acute, but prolonged at tip. Plumpness—slight wrinkling due to prominent veins. Pellicle—very little pubescence. Color—Light Brown, Plate 5, A-12. Flavor—good. Texture—firm.

Resistance to insects and diseases: Same as "Nonpareil," as determined from comparison with other varieties grown under comparable cultural conditions at Escalon, California.

I claim:

A new and distinct variety of almond tree, substantially as herein shown and described, characterized particularly as to novelty by the general similarity of the plant, blooms and nuts to those of the variety "Nonpareil" (unpatented), combined with later-blooming and later nut-ripening habits, and smoother and harder nut shells.

No references cited.